United States Patent
Lin et al.

(10) Patent No.: US 7,615,369 B2
(45) Date of Patent: Nov. 10, 2009

(54) RECONFIGURABLE PROTEIN PATTERNING USING ELECTROWETTING MICROELECTRODES

(75) Inventors: Chih-Tin Lin, Ann Arbor, MI (US); Amaya Frost, Huntington, NY (US); Edgar Meyhöfer, Ann Arbor, MI (US); Katsuo Kurabayashi, Ann Arbor, MI (US); Chao Yung Fan, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 351 days.

(21) Appl. No.: 11/233,975

(22) Filed: Sep. 22, 2005

(65) Prior Publication Data

US 2006/0063207 A1    Mar. 23, 2006

Related U.S. Application Data

(60) Provisional application No. 60/612,269, filed on Sep. 22, 2004.

(51) Int. Cl.
*C12M 1/34* (2006.01)
(52) U.S. Cl. ............ 435/287.1; 435/6; 435/285.2; 422/52; 422/82.08; 436/518; 436/524; 436/534; 436/172
(58) Field of Classification Search ............ 436/518, 436/524, 534, 172; 422/52, 82.08; 435/6, 435/287.1, 287.2, 285.2
See application file for complete search history.

(56) References Cited

U.S. PATENT DOCUMENTS

| | | | |
|---|---|---|---|
| 2001/0021534 A1* | 9/2001 | Wohlstadter et al. | 436/518 |
| 2002/0050611 A1* | 5/2002 | Yitzchaik et al. | 257/315 |
| 2002/0185184 A1* | 12/2002 | O'Connor et al. | 137/822 |
| 2003/0006143 A1* | 1/2003 | Banerjee et al. | 205/414 |
| 2003/0194709 A1* | 10/2003 | Yang | 435/6 |
| 2004/0077074 A1* | 4/2004 | Ackley et al. | 435/287.2 |

OTHER PUBLICATIONS

G. MacBeath, and S. L. Schreiber, "Printing Proteins as Microarrays for High-Throughput Function Determination," Science vol. 289, pp. 1760-1763 (2000).
E. P. Ivanova, J. P. Wright, D. Pham, L. Filipponi, A. Viezzoli, D. V. Nicolau, "Polymer Microstructures Fabricated via Laser Ablation Used for Multianalyte Protein Microassay," Langmuir vol. 18, pp. 9539-9546 (2002).
B. Shapiro, H. Moon, R. Garrell, and C. J. Kim, "Modeling of Electrowetted Surface Tension for Addressable Microfluidic Systems: Dominant Physical Effects, Material Dependences, and Limiting Phenomena," Proc. of The Sixteenth Annual International Conference on IEEE The Micro Electro Mechanical Systems, Kyoto, Jan. 19-23, 2003, pp. 201-205.

(Continued)

*Primary Examiner*—N Yang
(74) *Attorney, Agent, or Firm*—Brooks Kushman P.C.

(57) ABSTRACT

A protein patterning electrode device consisting of capacitor microelectrode arrays coated with a protein non-adherent layer is provided. Operation of the electrode is based on a phenomenon called "electrowetting," where surface wettability can dynamically be controlled by varying the voltage across the device electrodes. When an electric field is applied across the electrode layers, the surface accumulates charge and becomes hydrophilic, binding the proteins to the surface via ionic bonding. Electrically controlling the amount of the surface charge permits controlled protein surface affinity. The device provides a means for reconfigurable protein patterning.

12 Claims, 14 Drawing Sheets

OTHER PUBLICATIONS

H. J. J. Verhijen and M. W. J. Prins, "Reversible Electrowetting and Trapping of Charge: Model and Experiments," Langmuir vol. 15, pp. 6616-6620 (1999.

S. K. Cho, S. Fan, H. Moon, and C. J. Kim, "Creating Transporting, Cutting and Merging Liquid Droplets By Electrowetting-Based Actuation: Towards Digital Microfluidic Circuits," Proc. of The Fifteenth IEEE International Conference on Micro Electro Mechanical Systems, Jan. 20-24, 2002, pp. 32-35.

D. Huh, A.H. Tkaczyk, J.H. Bahng, Y. Chang, H.-H. Wei, J.B. Grotberg, C.-J. Kim, K. Kurabayashi, and S. Takayama, "Reversible Switching of High-Speed Air-Liquid Two-Phase Flows Using Electrowetting-Assisted Flow-Pattern Change," J. Am. Chem. Soc. vol. 125, pp. 14678-14679 (2003).

A. Frost, C.-T. Lin, E. Meyhofer, and K. Kurabayashi, "Electrically Tunable, Reprogrammable Protein Patterning Using Fluorocarbon Polymer-Coated Electrode Patterns," Proceedings of 8th International Symposium on Micro Total Analysis Systems (mTAS), vol. 2, pp. 112-114, Malmo, Sweden, Sep. 26-30, (2004).

J. D. Hoff, L.-J. Cheng, E. Meyhofer, L. J. Guo, & A. J. Hunt, "Nanoscale Protein Patterning by Imprint Lithography," Nano Letters vol. 4(5), pp. 853-857 (2004).

K.-B. Lee, S.-J. Park, C. A. Mirkin, J. C. Smith & M. Mrksich, "Protein Nanoarrays Generated by Dip-Pen Nanolithography," Science vol. 295, pp. 1702-1705 (2002).

J. Wright, E. Ivanova, D. Pham, L. Filipponi, A. Viezzoli, K. Suyama, M. Shirai, M. Tsunooka, and D. V. Nicolau, "Positive and Negative Tone Protein Patterning on a Photobase Generating Polymer," Langmuir vol. 19, pp. 446-452 (2003).

D. L. Huber, R. P. Manginell, M. A. Samara, B. Kim, B. C. Bunker, "Programmed Adsorption and Release of Proteins in a Microfluidic Device," Science, vol. 301, pp. 352-354 (2003).

J. W. Lussi, et al, "Selective Molecular Assembly Patterning at the Nanoscale: a Novel Platform for Producing Protein Patterns by Electron-Beam Lithography on SiO2/Indium Tin Oxide-Coated Glass Substrates," Nanotechnology, vol. 16, pp. 1781-1786 (2005).

E. A. Roth, et al, "Inkjet Printing for High-Throughput Cell Patterning," Biomaterials vol. 25, pp. 3707-3715 (2004).

K. F. Bohringer, et al, Infrared Light Induced Patterning of Proteins on ppNIPAM Thermoresponsive Thin FilmsL a "Protein Laser Printer," Proc. of IEEE Conference on Micro Electro Mechanical Systems (MEMS), Istanbul, Turkey, Jan. 22-26 (2006).

K. F. Bohringer, "Surface Modification and Modulation in Microstructures: Controlling Protein Adsorption, Monolayer Desorption and Micro-Self-Assembly," J. Micromech. Microeng. vol. 13, pp. S1-S10 (2003).

N. Y. Lee, J.R. Lim, Y.S. Kim, Selective patterning and immobilization of biomolecules within precisely-defined micro-reservoirs, Biosensors and Bioelectronics, vol. 21 pp. 2188-2193 (2006).

A. J. Sloane, J. L. Duff, N. L. Wilson, P. S. Gandhi et.al., "High Throughput Peptide Mass Fingerprinting and Protein Macroarray Analysis Using Chemical Printing Strategies," Molecular and Cellular Proteomics 1.7, pp. 490-499 (2002).

* cited by examiner

RECONFIGURABLE PROTEIN PATTERNING USING ELECTROWETTING MICROELECTRODES

CROSS-REFERENCE TO RELATED APPLICATIONS

This application claims the benefit of U.S. provisional application Ser. No. 60/612,269 filed Sep. 22, 2004.

STATEMENT REGARDING FEDERALLY SPONSORED RESEARCH OR DEVELOPMENT

The invention was made with Government support under Contract No. N66001-02-C8039. The Government has certain rights to the invention.

BACKGROUND OF THE INVENTION

1. Field of the Invention

The present invention is directed to protein patterning through application of an electric charge to a surface having no or minimal attraction for proteins, and to a method of protein patterning using such devices.

2. Background Art

Patterning of proteins is a useful technique with numerous applications, including biological sensors, bioanalyses, and as protein concentrators prior to analysis by other methods. Proteins can be patterned on surfaces to which they are adherent, and such methods have been widely used. One example is the deposition of bovine serum albumin (BSA) onto glass or silicone elastomer surfaces. By coating portions of these surfaces with coatings to which proteins do not adhere, protein patterns may be generated. However, the patterns thus produced are relatively permanent, i.e. not easily reversible.

Very few if any electrical methods exist for immobilizing proteins on a surface. Most of the existing methods are based on irreversible biochemical processes or surface chemistry occurring on photolithographically defined surface patterns. They require a new surface with all new photolithographic masks when a new pattern of proteins is desired. In that sense, the conventional approaches are "static" without providing a surface with the capability of patterning proteins in a reconfigurable manner. In other words, once a desired arrangement or protein is figured into the device design, it can not be changed.

Thermal methods that change a surface from a hydrophobic to a hydrophilic state have been used for protein patterning. In such methods, variation of temperature causes a change in the surface affinity of proteins. Proteins bound to a surface at elevated temperatures are released when the surface temperature is returned to room temperature. Such thermal methods are not useful when the orientation of the bound protein is important. Moreover, these methods cannot control the amount of adsorbed protein as the entire surface becomes hydrophilic and so the proteins bind with a weak ionic bond. Accordingly, the amount of bound protein can not be controlled using this method in that proteins either bind and cover the surface entirely or do not. Precise control of the temperature is necessary to ensure that denaturing of the proteins does not occur. Since the thermal method involves only a weak bond, its protein binding mechanism is highly susceptible to molecular diffusion processes. It follows that surface-bound proteins could be quickly replaced with proteins of higher molecular weight. In contrast, our method ensures that proteins remain in place without being affected by introducing other proteins. Once they are bound under an applied voltage a strong ionic bond is formed and the proteins can be released when the voltage is turned off through diffusion.

Accordingly, it is desirable to develop new methods and devices for preparing protein patterns, particularly protein patterns which are susceptible to ready protein removal, and in particular to provide devices which are reconfigurable to protein patterning.

SUMMARY OF THE INVENTION

It has now been surprisingly and unexpectedly discovered that protein patterning can be easily achieved by providing a surface which is substantially non-adherent to proteins, but which is capable of acquiring an electrical charge. Upon charging the surface, protein molecules become reversibly bound, the binding of which can be changed by lowering the electrical charge, removing the electrical charge, or reversing the electrical charge. The devices of the subject invention contain a first conductive electrode below the protein non-adherent and non-conductive layer, preferably immediately below, and a second conductive electrode above the surface. A passageway, channel, well, etc., is adjacent the protein non-adherent surface, and between the first and second conductive electrodes. When a potential difference (voltage) is applied between the first and second electrodes, a charge accumulates on the protein non-adherent surface(s), and proteins are now attracted to and adhere to these surface(s) from the protein-containing composition in the channel, well, etc. Differential adherence may take place in instances where there are two non-adherent surfaces, one bearing a positive charge and one bearing a negative charge, depending on whether proteins of an opposite charge are available. Upon decrease of the electric charge to a low level, preferably no charge, or by reversal of the electric charge, protein adherence is reversed also. Protein charge may be changed by standard techniques such as by control of pH.

The present invention provides in at least one embodiment a protein pattern device that includes at least one surface to which proteins are substantially non-adherent in the medium being used, but which adhere to this (these) surface(s) upon application of an electric field between conductive electrodes on either side of the surface. Proteins from a liquid media then adhere to the resulting charged surface, and may remain on the surface, or may be removed by lowering or reversing the applied potential. Proteins having two active sites of opposite charge may be made to adhere at a single surface at only one molecular site, the remaining site being available in the solution. The surfaces may be patterned as merely a uniform surface, or in any random or geometric form, for example as a matrix of dots, stripes, circles, etc.

The devices of the present invention may be "single layer" devices, i.e. devices which contain a single channel, well, etc. in which the protein composition will be contained, one or two ordinary non-adherent surfaces, and at least two conductive electrodes positioned outside these surfaces with respect to the cavity for the protein composition. Such "single layer" devices may be adapted for a single "static" loading of protein composition, or may be adapted to flow the composition through the cavity continuously or discontinuously. The present invention also embraces multilayer electrode devices.

In another embodiment of the present invention, an electrode system for protein patterning is provided. The system of this embodiment comprises a first electrode containing structure that includes a patterned conductive layer. The patterned conductive layer has a first region which is part of an active electrode and a second region which is part of an inactive electrode. The electrode system further comprises one or more dielectric layers disposed over the patterned conductive layer. The dielectric layer furthest from the patterned conductive layer is a top dielectric layer. The electrode system of this embodiment also includes an amphilic copolymer or polymer coating at least a portion of the top dielectric layer.

DETAILED DESCRIPTION OF THE PREFERRED EMBODIMENT(S)

Reference will now be made in detail to the presently preferred compositions or embodiments and methods of the invention, which constitute the best modes of practicing the invention presently known to the inventors.

In one embodiment of the present invention, devices that include at least one surface to which proteins are not substantially adherent are provided. Such surfaces are in general highly hydrophobic and non-polar. The non-adherent nature with respect to any particular protein can be assessed by contacting such a surface with a protein-containing solution, emulsion, or dispersion, removing the composition, and analyzing the surface for bound protein. Analysis can be conducted by standard techniques such as by tagging the protein with a fluorescent dye and monitoring the fluorescence of the surface. Preferably, less than 10% of the protein will adhere to the surface, more preferably less than 5%, and most preferably less than 1%. The surface is then provided with an electrical charge and the protein adherence measured. The adherent protein should be greater under these conditions, preferably by a factor of 5 or more, more preferably 10 or more. Most preferably, substantially no protein should adhere in the absence of an electrical field.

The non-adherent surface is preferably a fluorinated polymer surface, for example a fluorocarbon polymer, but other surfaces which have been rendered non-adherent by customary techniques can also be used. Examples include surfaces of glass, organopolysiloxane, metals, etc. which have been treated to make proteins non-adherent. Suitable coating agents are fluorinated hydrocarbon-functional silanes, alkylsilanes, and the like. Certain polymers such as polyolefins may be used with some proteins.

Figure 1:
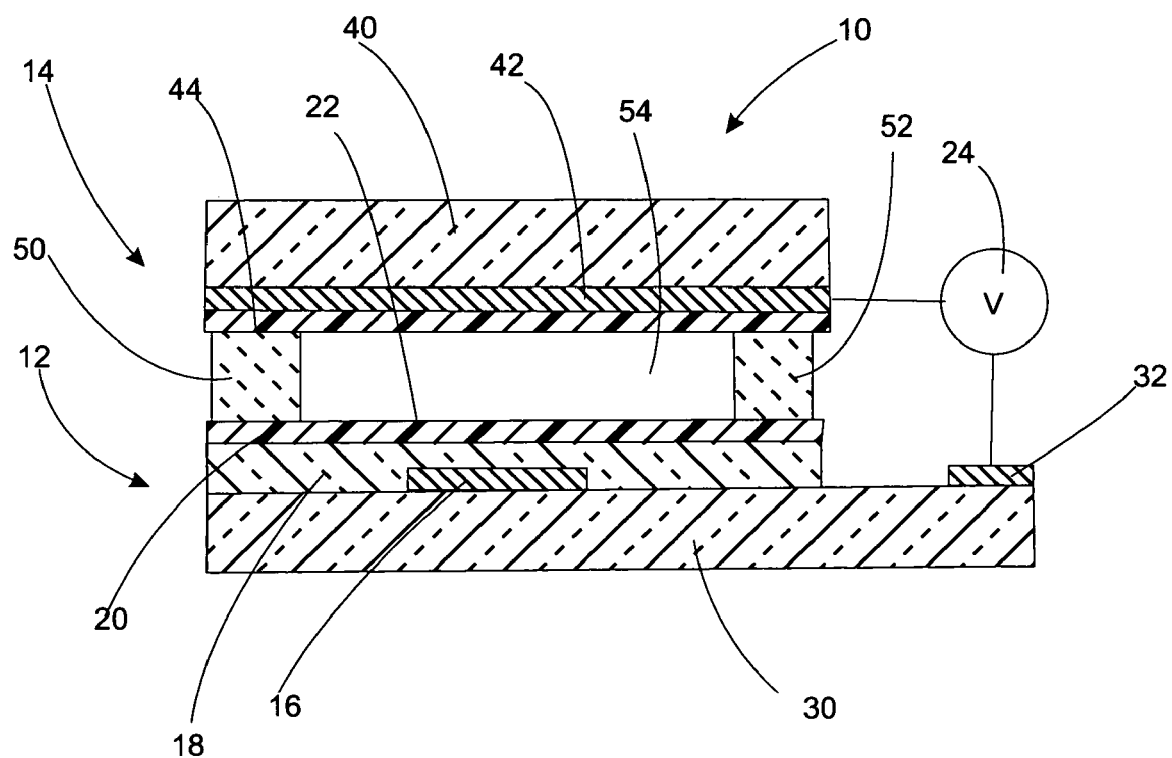
FIG. 1 is a cross-sectional schematic of an embodiment of the protein patterning electrode system of the invention.

With reference to FIG. 1 a schematic of an embodiment of the present invention is provided. Electrode system 10 includes at least two capacitive electrodes. Specifically, electrode system 10 includes first electrode containing structure 12 and second electrode containing structure 14. First electrode containing structure 12 includes patterned conductive layer 16 (i.e., an electrode) and an optional insulating layer 18 disposed over patterned conductive layer 16. First electrode containing structure 12 further includes non-adherent layer 20 which is in turn disposed over conductive layer 16 or insulating layer 18 if present. Non-adherent layer 20 also includes non-adherent surface 22 which is substantially non-adherent to proteins when non-adherent layer 18 is uncharged. However, non-adherent layer 18 is capable of acquiring an electric charge or of being polarized. Electrode system 10 also includes power supply 24 in communication with the first electrode containing structure and the second electrode containing structure. First electrode containing structure 12 and second electrode containing structure 14 are positioned relative to each other to allow contacting of non-adherent layer 18 with a protein composition. Characteristically, application of a potential difference between first electrode containing structure 12 and second electrode containing structure 14 renders non-adherent layer 18 adherent to protein molecules. The electrode devices of the present embodiment may be made to virtually any predetermined size. Accordingly, the devices of the invention range from microfluidic devices where solution volumes are measured in nanoliters to microliters, or macrofluidic devices where solution volumes are in the milliliter range.

In one variation, first electrode containing structure 12 includes a substrate 30 on which a conductive layer 16 and contact pads 32 are patterned. Patterning is accomplished by methods known to those in the art and include masking, selective deposition, lithography, image reversal lithography, wet etching, reactive ion etching, and the like. Suitable substrates include, but are not limited to, glass, ceramics, metal, plastics, and the like. Suitable materials for the conductive layer include, metals and transparent conductors (e.g., indium tin oxide (ITO), fluorine doped tin oxide, antimony doped tin oxide, etc.). Substrate 30 is optionally coated with insulating layer 18 which covers conductive layer 16 and exposed surface of substrate 30. An example of useful materials for insulating layer 18 include silicon nitride, silicon oxide, and other insulating oxides such at titanium oxide. Suitable materials from which non-adherent layer 20 is formed include but are not limited to polymers. Examples of useful polymers include fluorinated polymers and polyolefins. A particularly useful fluorocarbon polymer is CYTOP. CYTOP is an amorphous fluorocarbon polymer made by Asahi Glass Company. The specific name of CYTOP is Poly1,1,2,4,4,5,5,6,7,7-decafluoro-3-oxa-1,6-heptadiene. It is obtained by cyclopolymerization of perfluoro(alkenyl vinyl ether). The ring structure in the polymer main chain gives CYTOP amorphous morphology with visible transparency and solubility in some fluorine-containing solvents. In a specific example, substrate 30 is covered with a 0.3 µm thick silicon nitride layer and a 0.7 µm thick fluorocarbon polymer. Via-groves are etched through these layers to open the area covering the contact pads to provide electrical access from external circuits. In this variation, second electrode containing structure 14 includes substrate 40 which is covered with conductive layer 42 and non-adherent layer 44. The details of the substrate 40 are the same as substrate 30, conductive layer 42 is the same as layer 16, and non-adherent layer 44 is the same as layer 20. In a specific example, second electrode containing structure 14 is a slide glass substrate with a 0.12 μm thick blanket ITO layer and a 1.3 μm thick CYTOP coating. Glass spacers 50, 52 separate first electrode containing structure 12 and second electrode containing structure 14 to form flow chamber 54. In a specific example, spacers with a thickness of 500 μm are used. Conductive layer 42 forms the counter capacitor electrode to the electrode (layer 16) patterned on first electrode containing structure 12. The two sides of the flow chamber 50 are hermetically sealed to ensure that no liquid from the chamber comes in contact with the electrical connections. Sealing is accomplished with an adhesive or sealant such as wax.

In another embodiment of the invention, a method for protein patterning on a surface with the electrode patterning systems of the invention are provided. With reference to FIG. 1, non-adherent surface 22 of non-adherent layer 20 is contacted with a protein-containing composition. Application of a potential difference between the first electrode containing structure 12 and second electrode containing structure 14 render at least a portion of non-adherent surface 22 adherent to protein molecules. It should be appreciated that the adherence properties of the protein molecules may depend on the chemical structure of the protein molecules. Useful protein-containing compositions include, but are not limited to, protein-containing solutions, protein-containing emulsions, or protein-containing dispersions. The method of this embodiment is further characterized in that reversing the potential difference between first electrode containing structure 12 and second electrode containing structure 14 decreases adhesion of protein to non-adherent surface 22. The voltage applied to the electrodes is not critical, so long as it is of a magnitude whereby proteins become inherent to the normally non-adherent surface(s). The minimum voltage can easily be determined by examining the fluorescence of stained protein molecules at various voltage levels. In general, voltages of from 0.1 to 1000 volts or more are useful. Voltages in the range of 1 volt to 100 volts, more preferably 1 volt to 10 volts may be sufficient in many instances.

The method of this embodiment is particularly useful for concentrating dilute protein-containing compositions. Specifically, such concentration is achieved as follows. A first volume of a relatively dilute protein-containing composition is contacted with first electrode containing structure 12 at a predetermined potential difference such that protein adheres to the non-adherent surface. After a predetermined period of time, the adhered protein is released from non-adherent surface 22 by reversing or decreasing the potential difference. Concentration is increased since the releasing of the protein is into a second volume that is smaller than the first volume. Such concentration methodology is useful in chromatographic pre-concentrator applications and in Lab-on-a-chip type analysis systems. Specifically, Lab-on-a-chip type analysis systems use small sample sizes but need sufficiently large concentrations. If a protein-containing solution is washed through the device with its electrode charged, it would pull the proteins out of the solution. When a sufficient amount is collected on the surface, it could then be released and passed through the circuit to an analysis section. This may also be used as a method for immobilizing proteins between separations. Typical protein separations consist of two orthogonal measurements, for example proteins are first separated based on mobility then based on mass.

In a specific example, a buffer solution containing protein is drawn into chamber 54 from one of its open ends while a voltage is applied across the capacitive electrodes—first electrode containing structure 12 and second electrode containing structure 14. This solution is allowed to sit for three minutes to allow for diffusion of the protein through the solution. It is then rinsed with an empty buffer to remove all the proteins unbound to the bottom electrode surface. Any proteins remaining bound to the surface are detected using a fluorescence microscope.

Although the present invention is not limited by any theory of operation, the present invention is believed to function by electrowetting. Electrowetting is a phenomenon where an external applied field lowers the interfacial energy at a solid-liquid boundary. The lowering of the interfacial energy causes liquid to spread on a solid surface. It is believed that this is due to an accumulation of charge at the solid surface. The charge orients the liquid molecules in proximity to the surface. An electrical field applied across the solid-liquid interface causes a hydrophobic solid surface to be hydrophilic. The adhesion of proteins to a surface requires overcoming the hydrophobic barrier near the surface. This is accomplished by applying an electric field across the interface. Once the hydrophobic barrier is overcome, the proteins are free to approach the surface where the accumulated charge offers ionic bonding sites. Proteins in solution will selectively stick to hydrophilic surface areas and will form an ionic bond there. The remainder of the surface where no voltage is applied finds few protein molecules, leading to suppression of non-specific protein binding that is required for proteins. When the voltage is removed, the proteins remain in place until a reverse voltage is applied. The proteins are then repelled from the surface and the surface returns to its original state. Electrowetting occurs regardless of the direction of the applied field. This indicates that we can accumulate both positive and negative surface charges. Switching the charge polarity will allow us to bind proteins directionally. In many cases, proteins are found to be bound to other proteins or ligands. These other proteins are used to assure the orientation of the desired protein in relation to the substrate surface. Our approach could be used to switch the orientation or protein molecules depending on their polarity.

Electrowetting experiments have shown that regardless of whether a positive or negative charge is accumulated on the surface, the total surface energy is lowered and becomes favorable for protein binding. This allows for conformational binding of motor proteins such as kinesin, which can be approximated as a dipole. The functional end of kinesin has a negative charge while the binding tail end has a positive charge. The protein will bind and still be functional only when the surface accumulates a negative charge. The protein may bind to a positively charged surface, however it may no longer be bound in such a way that its functional end is exposed for use.

Figure 2:
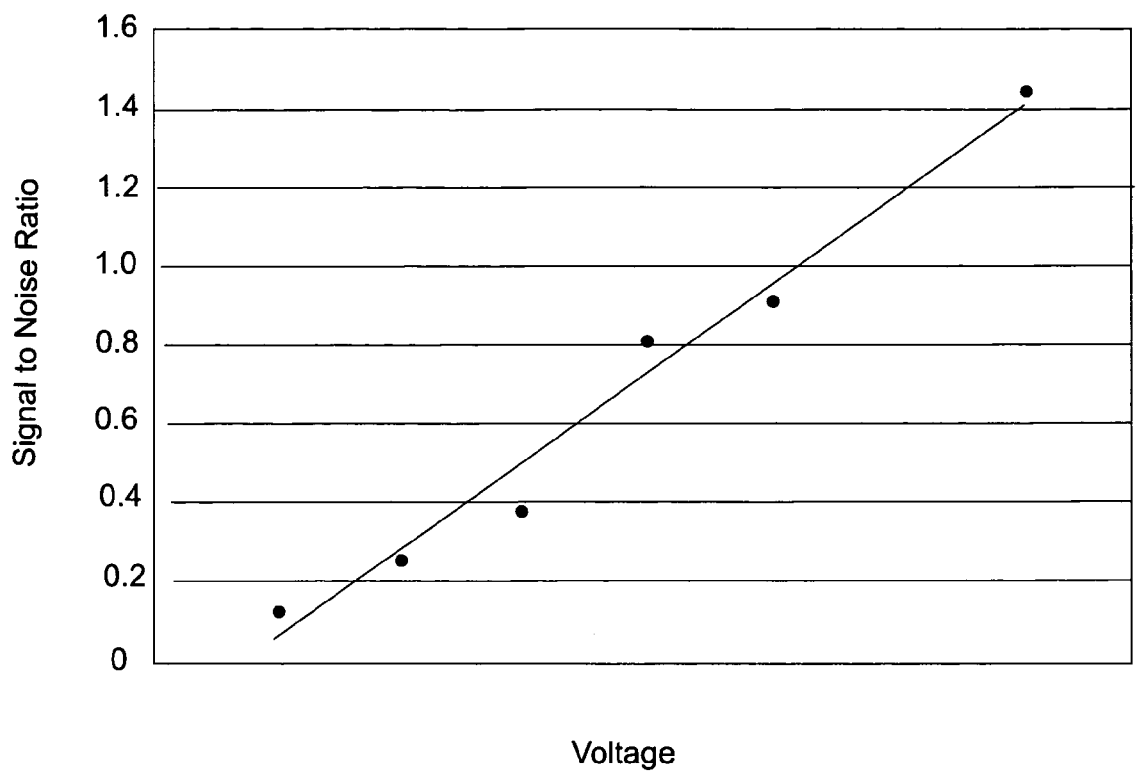
FIG. 2 is a plot of the fluorescent signal to noise ratio versus the applied voltage for a tris acetate buffer with a pH of 6.94.

The electrode system and method of the invention are tested using fluorescence microscopy. The protein tested is bovine serum albumin (BSA) which has been labeled with tetramethylrhodamine fluorescence dye. When exposed to green light ($\lambda=532$ nm) the labeled proteins emit a red florescent signal ($\lambda=630$ nm). The microscope has an optical filter covering the detector to allow only the light with wavelength near 630 nm through to the detector. This lowers the noise of the detection method. With reference to FIG. 2, a plot of the fluorescent signal to noise ration versus the applied voltage is provided. FIG. 2 indicates that a linear increase of protein population bound to the electrode surface with increasing voltages.

Figure 3:
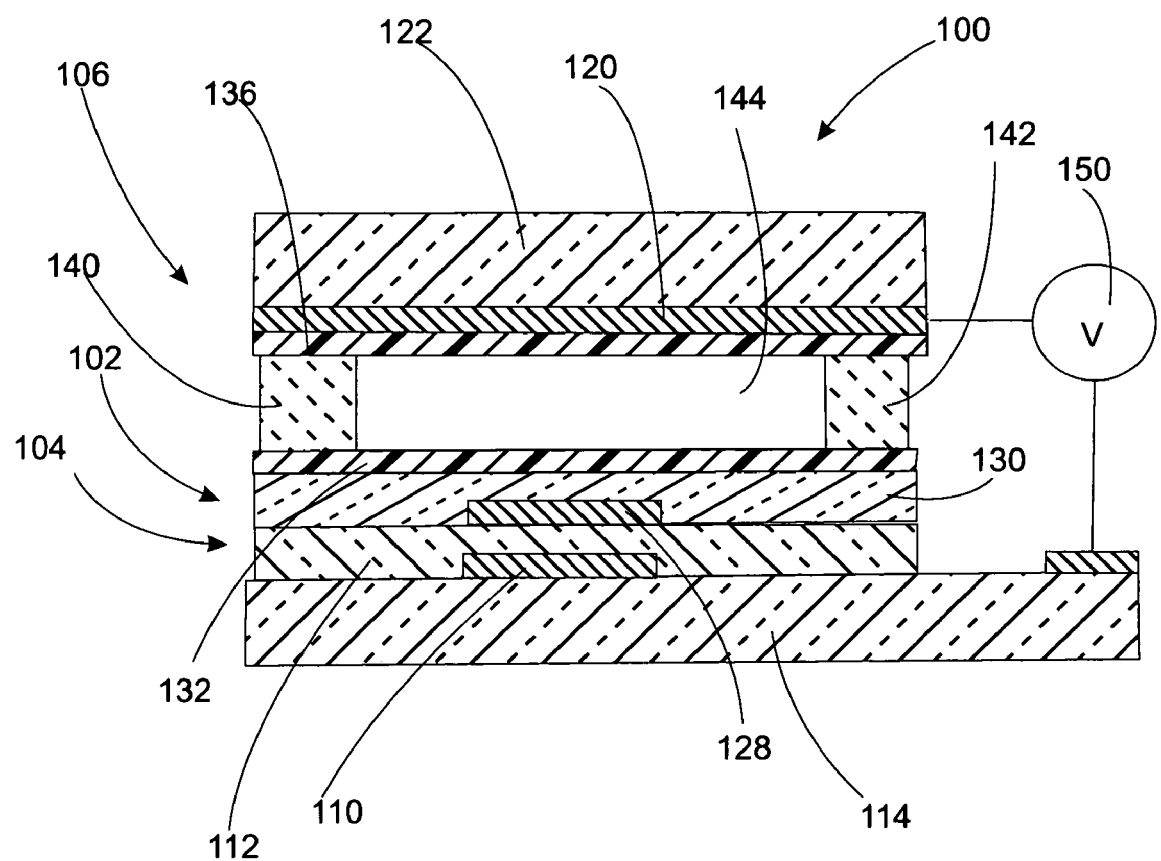
FIG. 3 is a cross-sectional schematic of another embodiment of the protein patterning electrode system of the invention.

With reference to FIG. 3, another embodiment of the present invention is provided. In this variation, electrode system 100 has a structure which is similar to a random access memory (RAM) structure in which charge is intentionally trapped inside a floating electrode. Electrode system 100 includes floating electrode containing structure 102 located between first electrode containing structure 104 and second electrode containing structure 106. In an analogous manner to the electrode system of FIG. 1, first electrode containing structure 104 includes patterned conductor 110 and insulating layer 112 disposed over substrate 114. Similarly, second electrode containing structure 106 includes conductive layer 120 and disposed over substrate 122. Floating electrode containing structure 102 is disposed over first electrode containing structure 104. Floating electrode containing structure 102 is formed by deposition of conductive layer 128 over first electrode containing structure 104 followed by overcoating with insulating layer 130. Non-adherent layer 132 is disposed over floating electrode containing structure 102 and non-adherent layer 136 is disposed over second electrode containing structure 106. Floating electrode structure 102 is separated from second electrode structure 106 with spacers 140, 142 to form flow channel 144 in an analogous manner as above. When electrode system 100 is charged by power supply 150, the charge is mirrored in the hydrophobic coatings, providing a similar response as described above. This ensures that the charge does not leak out of the capacitor, keeping the proteins from releasing from the surface over long periods of time. As a result, the device requires a small maintenance voltage after an initial voltage is applied to trap the charge, thus trapping the proteins permanently. The device would operate as RAMs with charge stored in a dielectric layers below a hydrophobic surface. The trapped charge changes the surface wettability and allows the proteins to come in contact with the surface and bind with the accumulated charge. Switching the polarity of the applied voltage allows for a purge of the trapped charge and release the bound proteins from the surface. Continuously applying the voltage with the opposite polarity would eventually rebind the proteins to the surface with its dipole moment flipped. Reprogrammable protein patterning is possible by repeated programming of the voltage pattern applied to the capacitor electrode arrays. The proposed programmable RAM protein device can be fabricated using similar processing used for the above-described device.

Figure 4:
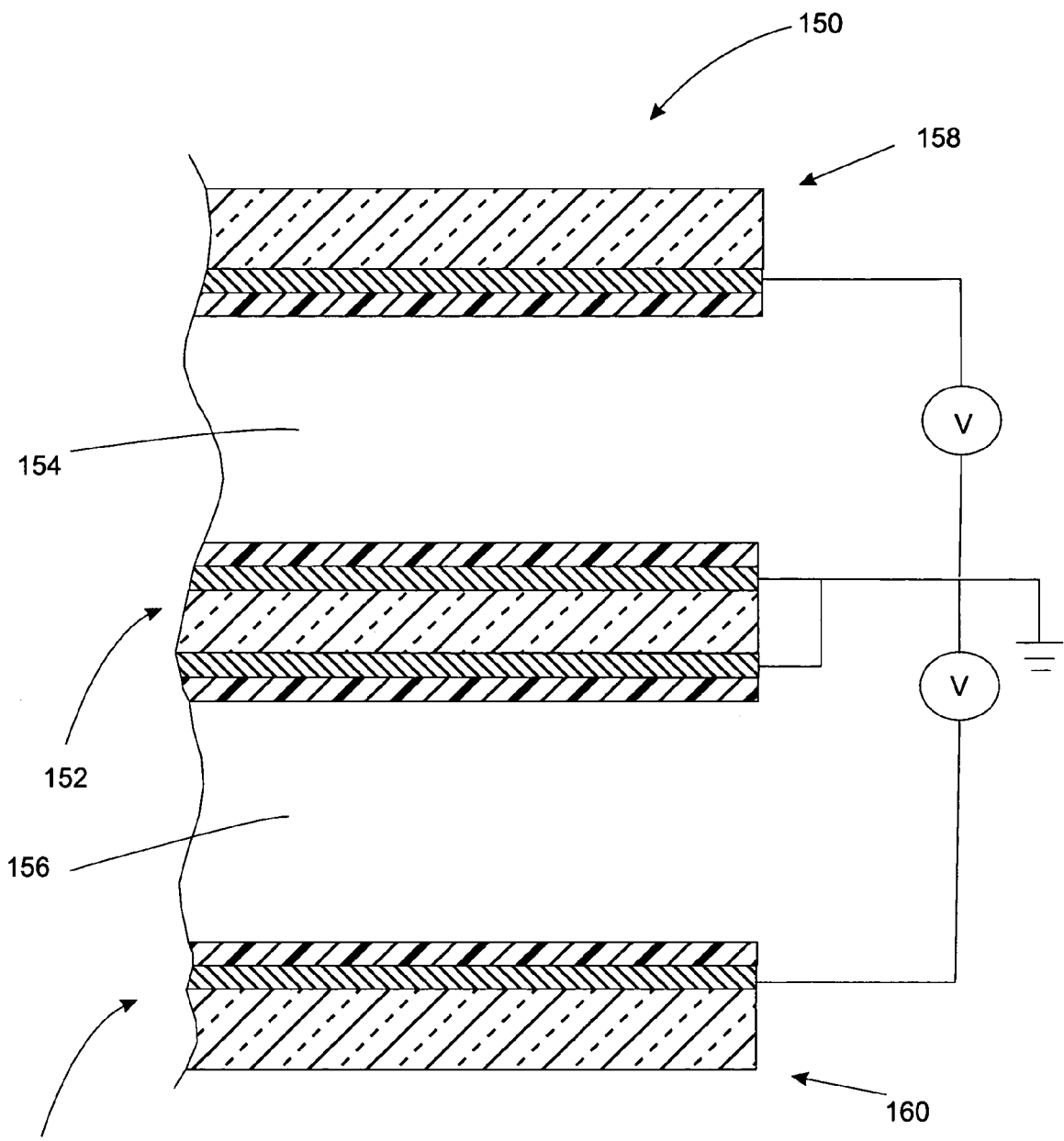
FIG. 4 is a cross-sectional schematic of a multicavity electrode system.

In another embodiment of the present invention, multilayer electrode devices are provided. Such devices have multiple cavities, preferably in parallel, although series arrangements are also possible. With reference to FIG. 4, electrode device 150 includes central conductive electrode structure 152 which functions as a conductive electrode for both of cavities 154, 156, with corresponding conductive electrode structures 158, 160 positioned outside and more remote from cavities 154, 156. Electrode structures 152, 158, 160 include the multilayer structure as set forth above but adapted for the configuration of electrode device 150. The multilayer structure of FIGS. 1 and 3 allow for a variety of biasing schemes. For example, the central electrode structure 150 may be maintained at ground (0 volts), and both "outside" electrodes may be maintained at a positive or at a negative voltage, the central electrode may be maintained at ground with one outside electrode being maintained at a positive potential and the other at a negative potential in relation to ground, one outside electrode may be maintained at ground, a central electrode at a higher or lower potential than ground, and the remaining outside electrode at a yet higher or a yet lower potential. Accordingly, it is the potential difference (voltage differential) between the layers which is important, and not the voltage at any particular conductive electrode.

Figure 5A:
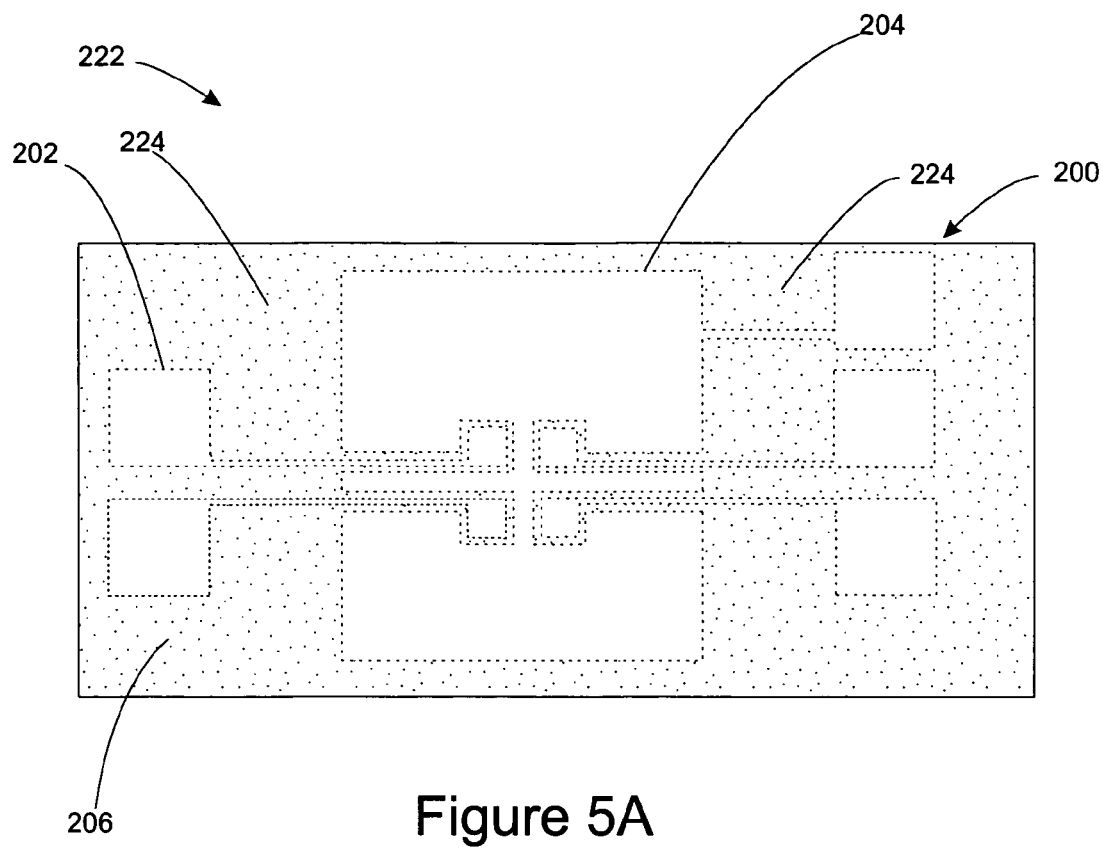
FIG. 5A is a top view of the patterning of active and inactive electrodes with a single electrode structure for a protein patterning electrode device.
Figure 5B:
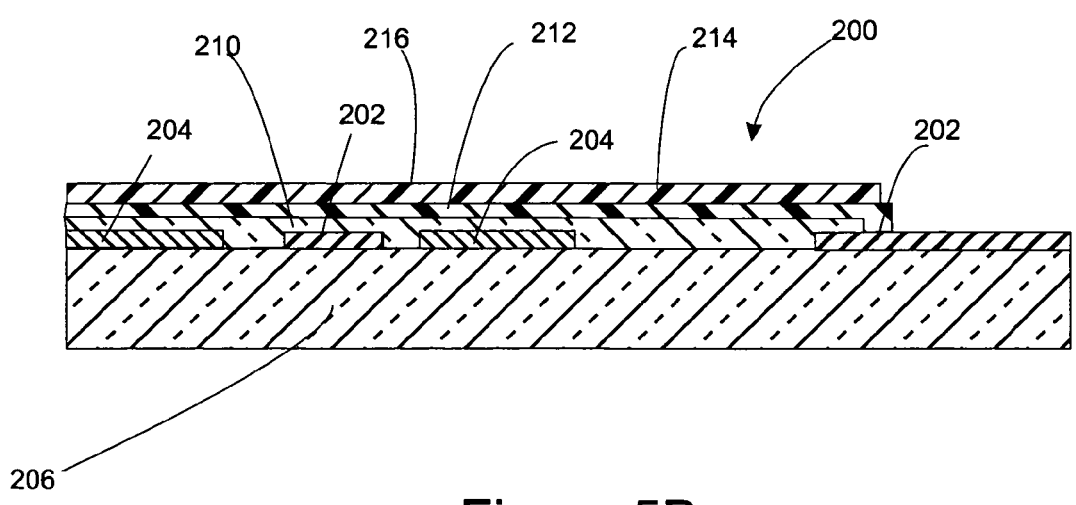
FIG. 5B is a side cross-sectional view of the electrode structure of FIG. 5A.

In still another embodiment of the present invention, a protein patterning electrode device having an electrode structure that includes both an active electrode and an inactive electrode is provided. With reference to FIGS. 5A and 5B, schematics of the electrode structure of this embodiment are provided. FIG. 5A is a top view of the patterning of the conductive layers in the electrode structure of this embodiment. FIG. 5B is a side cross sectional view of the electrode structure. Electrode structure 200 includes active electrode 202 and inactive electrode 204 each disposed over substrate 206. One or more dielectric layers are then disposed over active electrode(s) 202, inactive electrode(s) 204, and any exposed surfaces of substrate 206. In one variation, for example, insulating layer 210 is disposed over substrate 206 and electrodes 202 and 204. Typically, insulating layer 210 is made from silicon nitride, silicon oxide, or another metal oxide. PECVD is particularly useful for forming this layer. Intermediate polymer layer 212 is next disposed over substrate 206 covering electrodes 202 or 204 and/or insulating layer 210 if present. Next, top polymer layer 214 is disposed over intermediate polymer layer 212. In one variation, top polymer layer 214 is a non-adherent layer as described above.

Advantageously, in this embodiment, an amphilic polymer or copolymer is coated over portions of electrode structure 200. For example, in the variation described above, an amphilic polymer or copolymer is disposed over portions of surface 216. Pluronic copolymers are particularly useful for this purpose. Pluronic copolymers are non-ionic copolymers with hydrophobic and hydrophilic regions. Pluronic copolymers adsorbed on hydrophobic surfaces prevent proteins from binding to the surfaces. Moreover, Pluronic copolymers on hydrophilic surfaces do not prevent proteins from binding to those surfaces. A specific example of a useful polymer for intermediate layer 212 is Parylene. Since a hydrophobic dielectric layer can be switched to become hydrophilic when a voltage is applied across the dielectric layer (electrowetting phenomena), proteins can be controlled to bind or not to bind onto a hydrophobic dielectric surface coated with Pluronic copolymers by controlling whether a voltage drop is present or not across this hydrophobic dielectric layer. Pluronic copolymers are known to repel many types of proteins. Accordingly, once a condition is found to dynamically change Pluronic's protein repelling ability as described above, many different proteins can be dynamically patterned with the same conditions.

Figure 6:
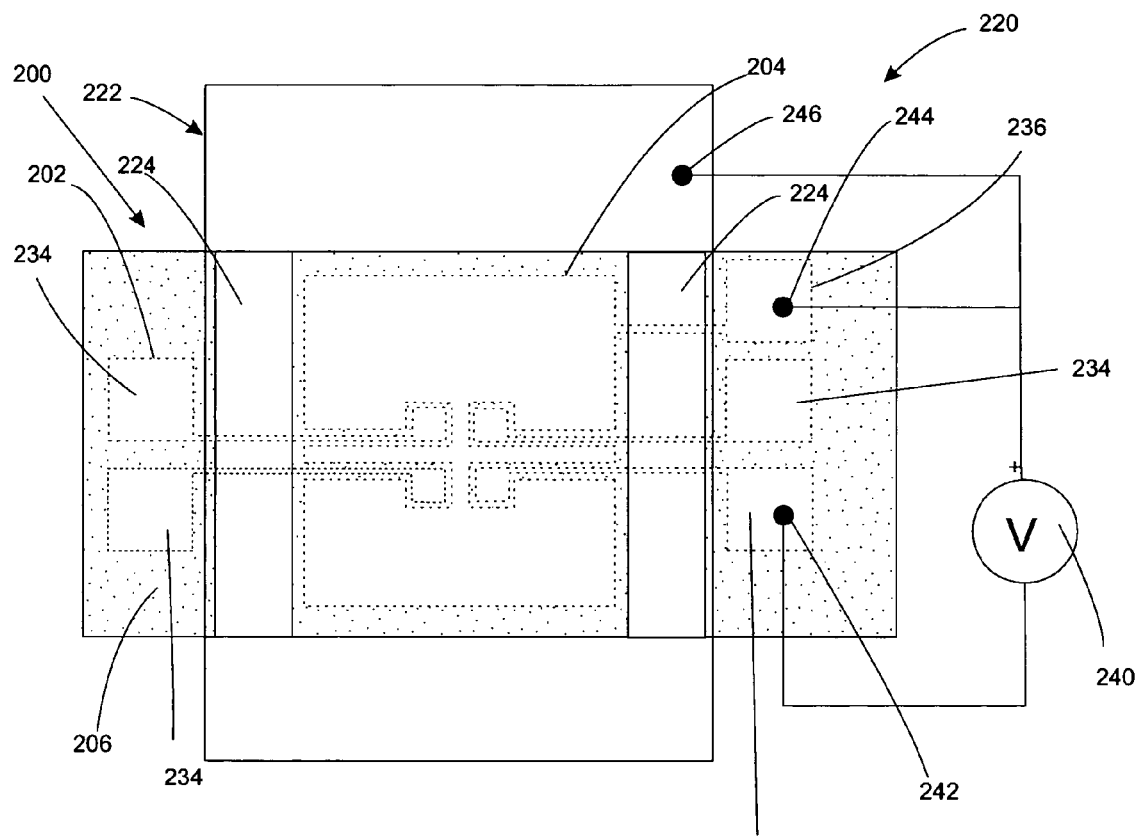
FIG. 6 is a top view of a protein patterning device incorporating the electrode structure of FIGS. 5A and 5B.
Figure 7:
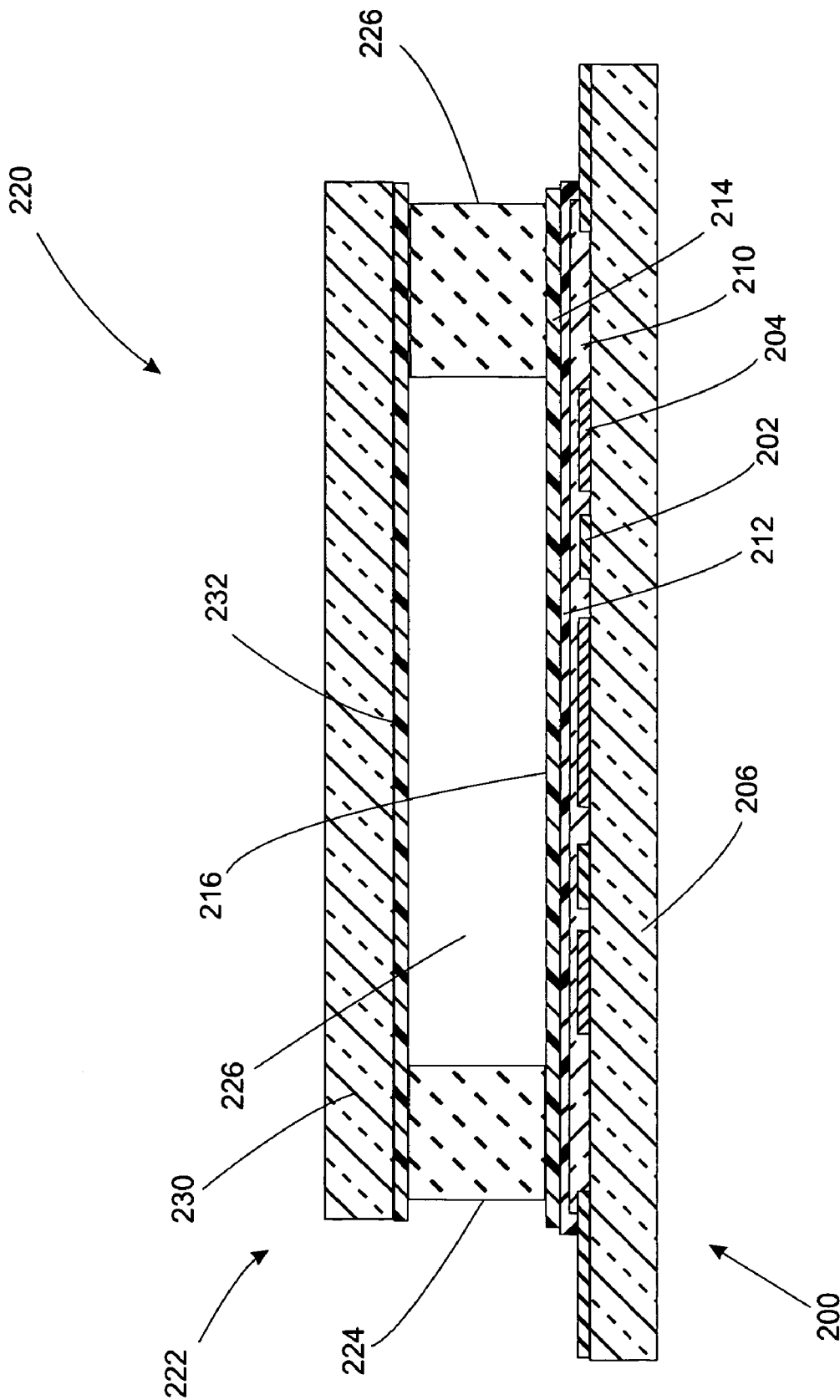
FIG. 7 is a cross-sectional schematic of a protein patterning device incorporating the electrode structure of FIGS. 5A and 5B.

With reference to FIGS. 6 and 7, a protein patterning device incorporating the electrode structure of FIGS. 5A and 5B is provided. FIG. 6 is a top view of a protein patterning device incorporating the electrode structure of FIGS. 5A and 5B. FIG. 7 is a cross-section of a protein patterning device incorporating the electrode structure of FIGS. 5A and 5B. Protein patterning device 220 includes electrode structure 200 and second electrode structure 222 which are separated by spacer 224 to form flow channel 226. Second electrode structure 222 includes substrate 230 and conductive layer 232. Device 220 also includes contact pads 234, 236 for attachment to a power supply. After coating with an amphilic copolymer or polymer, operation of electrode device 200 is the same as the operation of the devices set forth above. A voltage is applied to protein patterning device via power supply 240. Device 200 also includes contacts 242, 244, 246 for attachment to power supply 240. To let proteins adsorb onto active electrodes, a voltage drop should exist between the chamber solution and the active electrodes (in other words, voltage drop should exist across the dielectric layer on top of the active electrodes). This voltage drop across the dielectric on top of the active electrode turns the dielectric from being hydrophobic to being hydrophilic, thus, making Pluronic copolymers coated on top of this dielectric region to turn from repelling to not repelling proteins.

With reference to FIGS. 5A, 5B, 6 and 7, in order to ensure that proteins adsorb onto active electrodes 202, a voltage drop should exist between the chamber solution and the active electrodes (in other words, voltage drop should exist across the dielectric layers on top of the active electrodes). This voltage drop across the dielectric on top of the active electrode turns the dielectric from being hydrophobic to being hydrophilic thereby causing Pluronic copolymers coated on top of this dielectric region to turn from repelling to not repelling proteins. In order to make sure that proteins are repelled elsewhere (no protein binding elsewhere), inactive electrode(s) 204 are utilized. Inactive electrode(s) 204 cover the rest of the surface of device 200. The inactive electrode is shorted to the chamber solution via contacts 244, 246 so that no or minimal voltage drop should exist between the chamber solution and the inactive electrode (in other words, to have zero or minimal voltage drop across the dielectric layer on top of the inactive electrode). This zero or minimal voltage drop across this dielectric region should be low enough to not change the dielectric's initial hydrophobic state to that of hydrophilic. Accordingly, Pluronic copolymers coated on the inactive region do not change their ability to repel proteins and prevent them from binding to the surface.

Figure 8A:
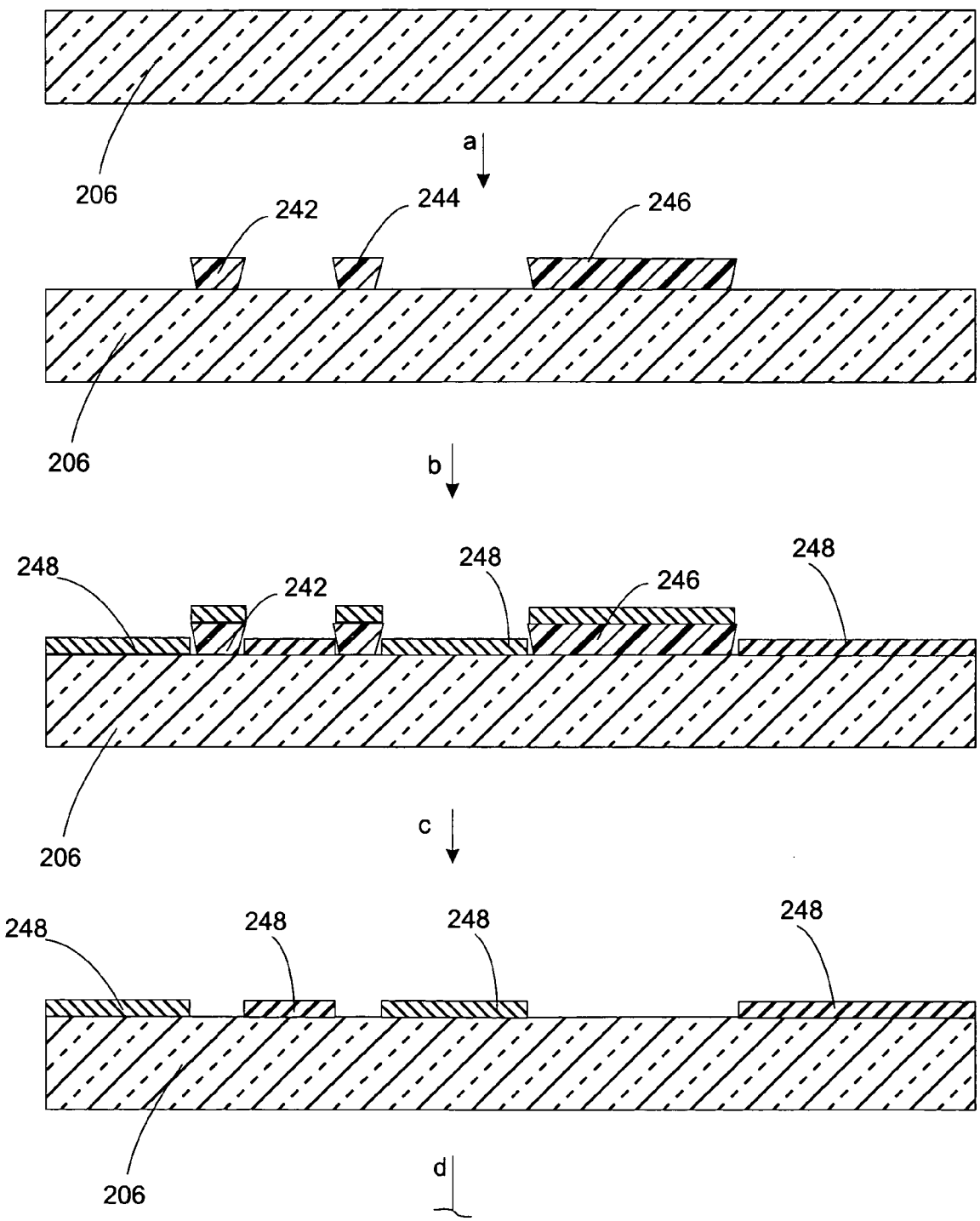
FIGS. 8A and 8B are schematic flow charts describing the fabrication of the electrode structure of FIGS. 5A and 5B.
Figure 8B:
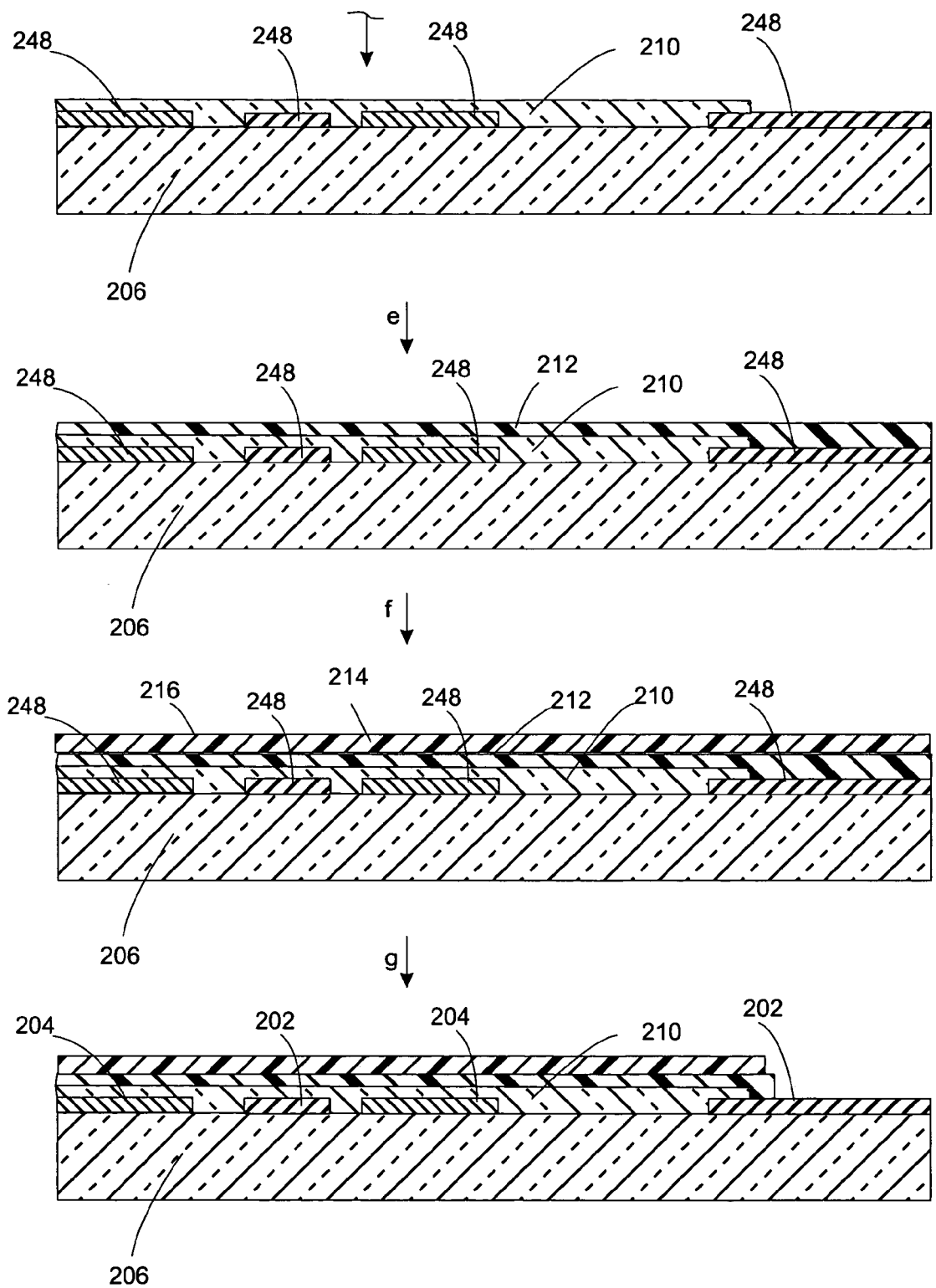

With reference to FIGS. 8A and 8B, schematic flow charts describing the fabrication of the electrode structure of FIGS. 5A and 5B is provided. Substrate 206 is first cleaned with a Pirahana clean. In step a) substrate 206 is patterned by image reversal lithography to produce masks 242, 244, 246 on substrate 206. In step b) a conductive layer 248 is deposited over substrate 206 and masks 242, 244, 246. Suitable electrically conductive layers are made from metals and transparent conducting oxides such as ITO and fluorine doped tin oxide. In step c) masks 242, 244, 246 are lifted off to reveal the conductive electrodes that ultimately become active electrode(s) 202 and inactive electrode(s) 204. In step d) first dielectric layer 210 is deposited over substrate 206 and conductive layer 248. A suitable dielectric layer is formed from silicon nitride and silicon oxide. This layer is advantageously deposited by PECVD. In step e) second dielectric layer 212 is deposited over first dielectric layer 210. This dielectric may be polymer-based or may be an insulating nitride or oxide such as those mentioned for the first dielectric layer. Parylene is a particularly useful polymer for this layer. In step f) non-adherent layer 214 is deposited over second dielectric layer 212. Non-adherent layer 214 is made from the material described above. CYTOP is particularly useful.

Figure 9:
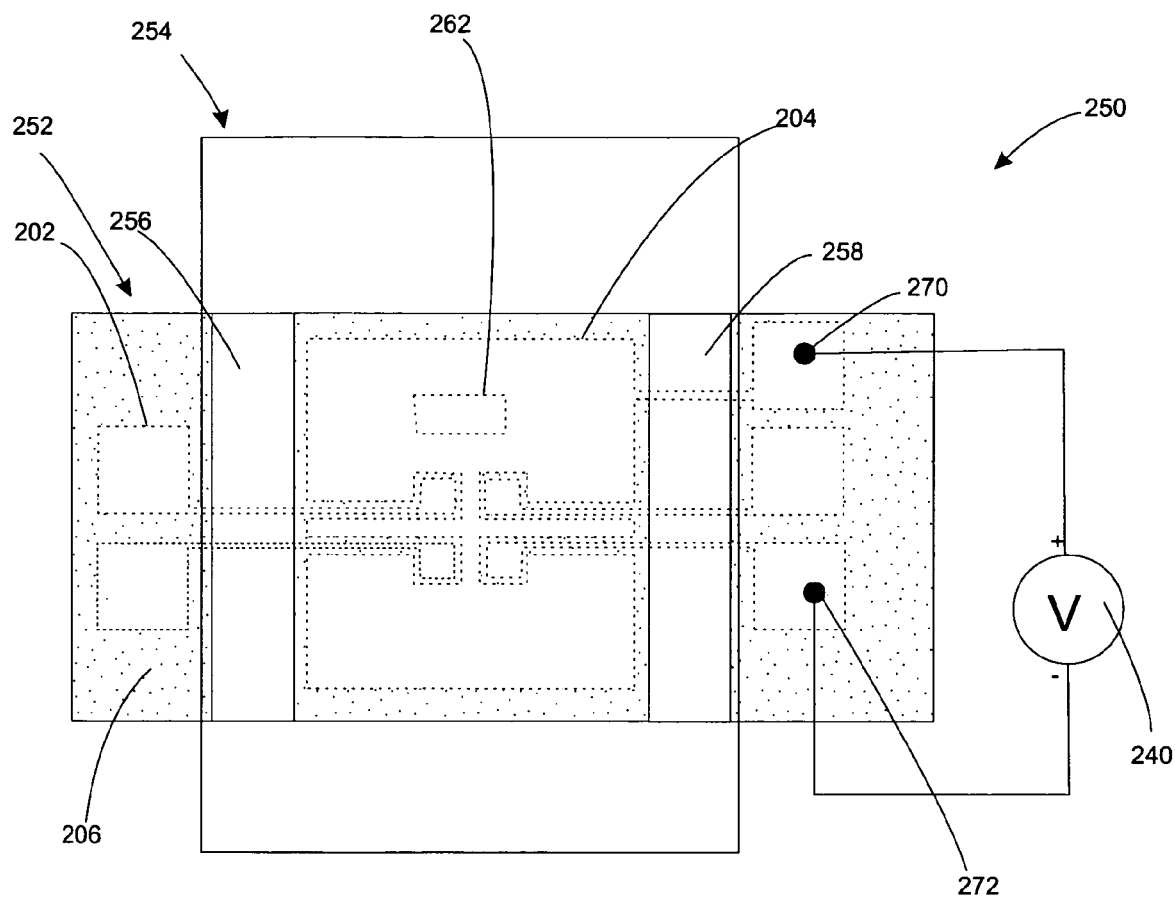
FIG. 9 is a top view of a protein patterning electrode system without a separate counter electrode.
Figure 10:
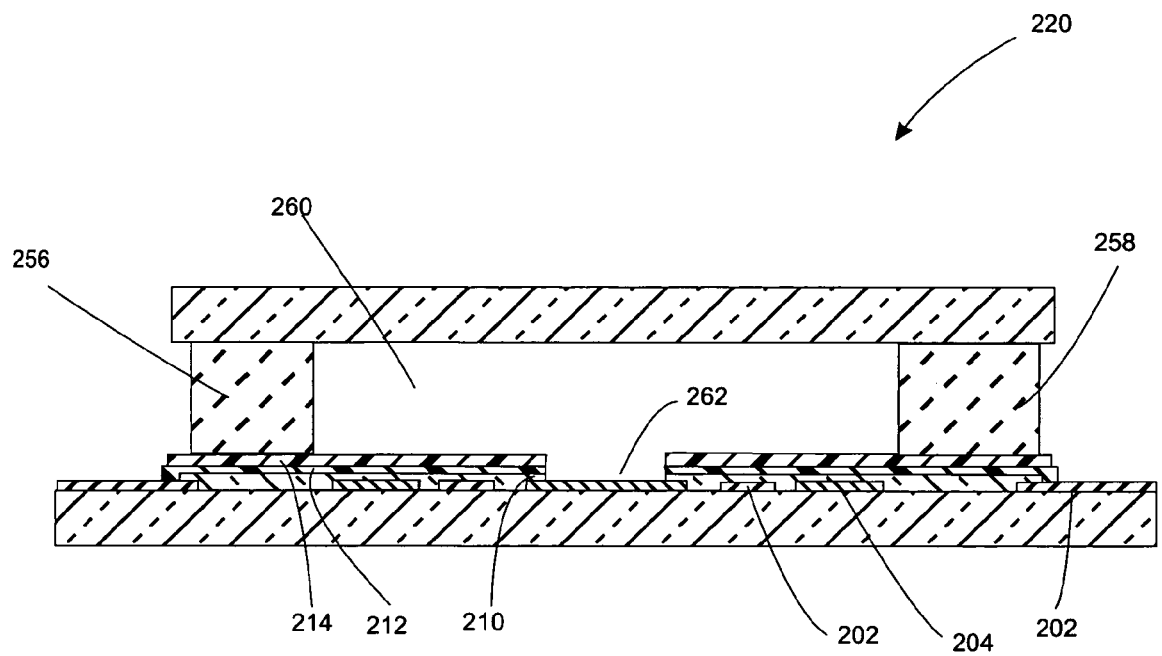
FIG. 10 is a side view of a protein patterning electrode system without a separate counter electrode.

With reference to FIGS. 9 and 10, a variation of the present embodiment without a counter electrode is provided. FIG. 9 is a top view of the device of this variation. FIG. 10 is a cross-sectional view of the device of this variation. Protein patterning device 250 includes electrode structure 252 and counter structure 254 which are separated by spacers 256, 258 to form flow channel 260. Electrode structure 252 is the same as electrode structure 200 of FIGS. 5A and 5B except as described below. Counter structure 254 includes substrate 206 but does not include a conductive layer and does not function as an electrode. Instead, electrode structure 252 has portion 262 of the inactive electrode exposed to solution in channel 258. Finally, device 250 also includes contacts 270, 272 for attachment to a power supply. Portion 262 of the inactive electrode is connected to one end of the power supply 240 via contact 270. Active electrode(s) 202 are connected to the other end of the power supply via contact 272. Since the inactive electrode is exposed and shorts to the chamber solution via the etched dielectric layer region on top of the inactive electrode, no counter electrode is needed. The electrode structure of this variation may be made by analogous method to that described in FIGS. 8A and 8B.

It should be noted that the electrode structures of FIGS. 5-8, include three dielectric layers—insulating layer 210, intermediate polymer layer 212, and top polymer layer 214. In variations of the invention, these layers can be replaced by any type of dielectric layers and any number of dielectric layers so long as the following conditions are met:
1) the dielectric combination can achieve device breakdown voltage higher than that of the device operation voltage
2) the dielectric combination has desired electrowetting effects (the dielectric surface touching the chamber solution can change from being hydrophobic to being hydrophilic) when a voltage is applied across the dielectric combination
3) the dielectric combination has a hydrophobic layer as its topmost layer (i.e., the layer that touches the chamber solution).

Moreover, these variations do not require that the dielectric layers be non-adherent to proteins, or be a polymer etc. as long as the chosen dielectric layer combination satisfies the above three conditions.

Figure 11A:
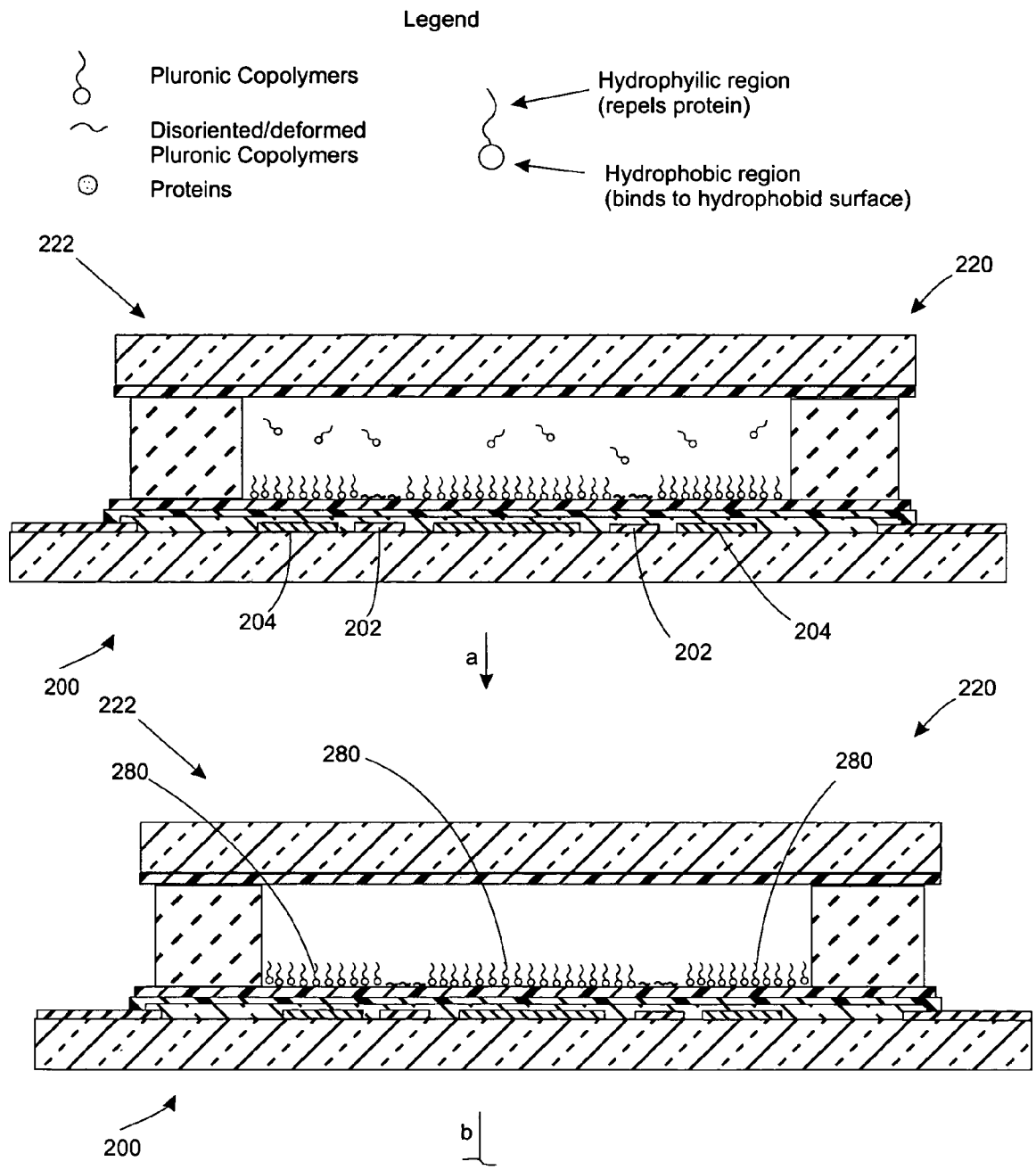
FIGS. 11A and 11B are a schematic flow chart showing switching using the electrode structures of FIGS. 5A. 5B, 6, and 7.
Figure 11B:
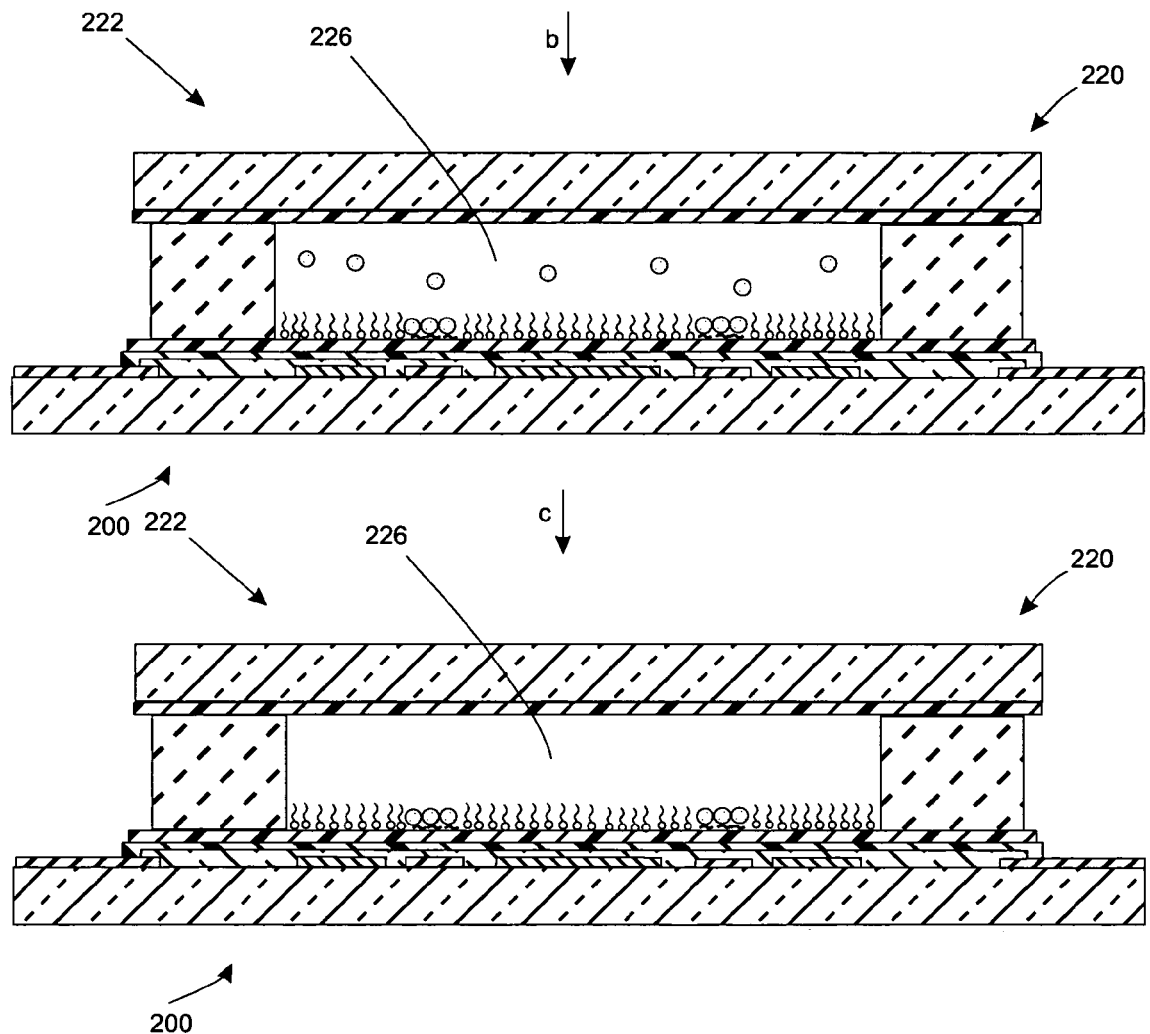

With reference to FIGS. 11A and 11B, a schematic flow chart showing switching (i.e., reconfigurable patterning) using the electrode structures of FIGS. 5A, 5B, 6, and 7 is provided. In step a) after protein patterning device 220 is suitably biased, a solution containing pluronic copolymer is introduced into flow chamber 226. Next in step a) excess Pluronic copolymers are washed away to leave Pluronic coating 280 that repels proteins on the inactive electrode regions. The Pluronic coating on top of the active electrodes loses its ability to repel proteins (could be either due to deformation or absence of the Pluronic molecules from the active region, which has turned hydrophilic by the voltage drop). In step b) a protein containing solution is introduced into flow chamber 226. Proteins are adsorbed on to the active electrodes and get repelled from the inactive electrode. In step c) excess proteins are away, leaving the proteins that were adsorbed on the active electrodes. An evidence showing that this Pluronic Switch Design works: microtubules are stuck on the active electrode. Since two proteins (microtubules and kinesins) were flown into the chamber, this picture indicates that either microtubules adsorbed directly onto the active electrode or kinesins (not fluorescently labeled) were adsorbed onto the active electrode and grabbed onto the microtubules in place. The electrode dimension is ~60 micrometer wide.

Figure 12:
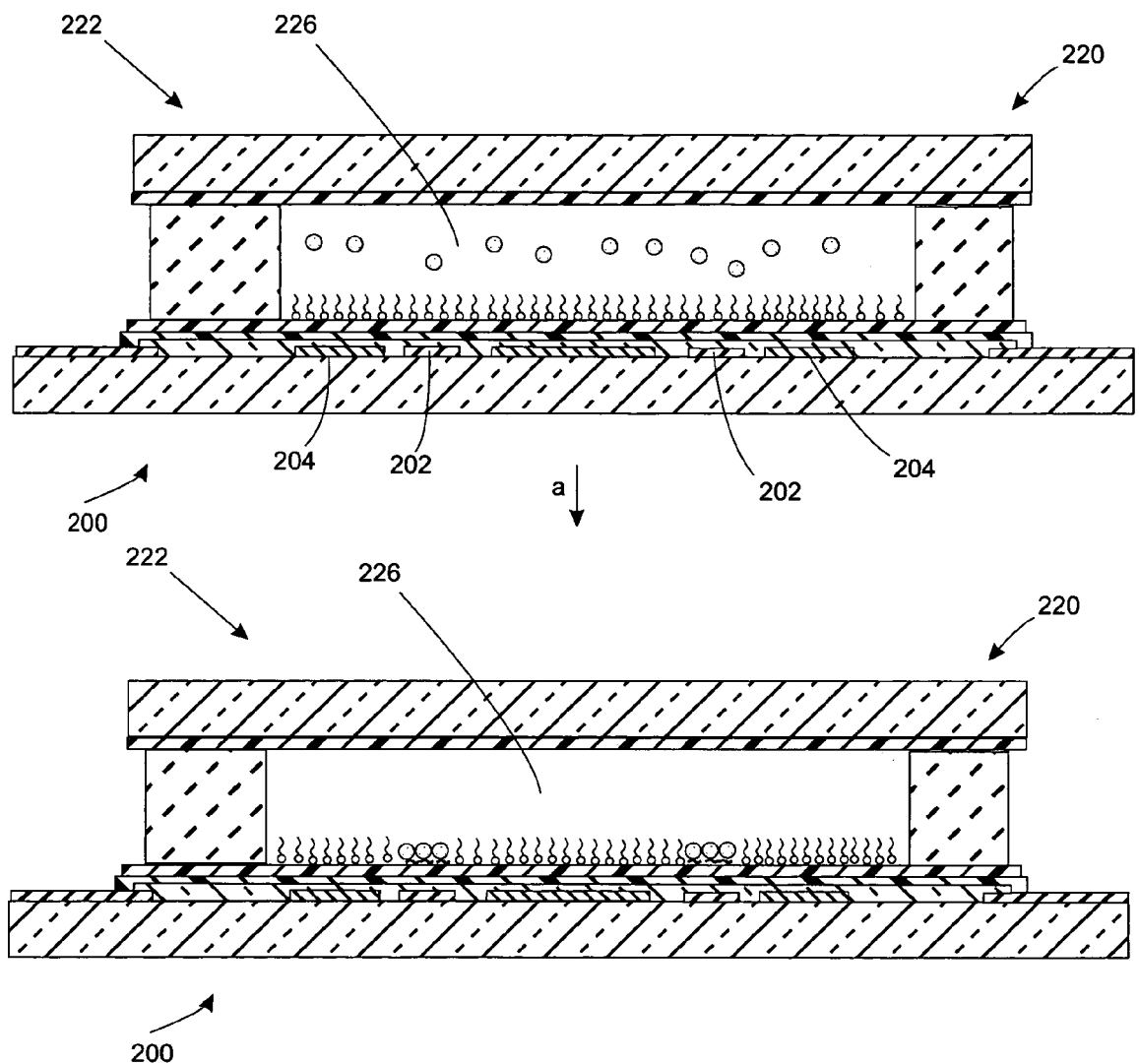
FIG. 12 is a schematic flow chart showing switching using the electrode structures of FIGS. 5A, 5B, 6, and 7.

With reference to FIG. 12, an alternative switching scheme of the electrode structures of FIGS. 5a, 5B, 6, and 7 is provided. Protein binding on the active electrodes can be reversed by either turning the voltage off or applying an appropriate reverse voltage. Such voltage adjustment enables dielectric on the active electrode region to turn from hydrophilic back to the initial hydrophobic state, thereby allowing Pluronic copolymers to be aligned in a way such that proteins get repelled from the surface. Accordingly, the active electrode region can be switched from protein binding to protein unbinding and vise versa, achieving a dynamic switchable protein patterning device. In step a) the voltage is turned off or reversed to make the dielectric on the active region to turn from hydrophilic back to its initial hydrophobic state with a concurrent reconfigurable binding of protein to the active electrodes.

In another embodiment of the invention, multiple proteins are adhered to a surface. Multiple protein patterning is achieved by first turning on one electrode and rinsing with a solution containing a first protein A, then rinsing with a buffer. A second electrode can be turned on, and a second solution containing a second protein B can be washed through the flow chamber. This will allow proteins A and B to be selectively patterned on the same chip surface.

In still another embodiment of the invention, the electrode device of the invention can be integrated with other MEMS components on a single chip, providing more flexibility for a biological MEMS sensor. For example, functional proteins such as antibodies could be selectively patterned at the ends of cantilever MEMS beams. In this manner on array of beams, each with a known antibody could be used to detect antigens. The proteins can be patterned using the electrowetting method and beam deflection can be monitored. In this manner, antigens can be detected and identified.

The protein patterning electrode devices of the present invention are advantageously applied to multi-step protein separation. Multi-step protein separation and, in particular, two-step protein separation processes present significant difficulty with regards to avoiding contamination from one separation to another. The devices of the present invention, immobilize proteins on a surface which may be selectively released and passed along to a second measurement section of the chip. Accordingly, two or more measurements can be performed on one chip without intervention by an operator to physically transfer samples from one separation tool to another. For example, if the first separation is performed by the isoelectric focusing (IEF), where proteins in a pH gradient separate to the pH at which their net charge is zero, the proteins can be immobilized on a first surface then selectively passed along to a channel for capillary electrophoresis, where the charge to mass ratio of the proteins is determined by measuring the travel time down a capillary. Accordingly, the present invention is particularly useful for protein separation and assays using lab-on-a-chip technology.

As set forth above, substrates useful for the subject invention devices are not limited, and may be metal, glass, plastic, etc. When metal substrates are employed, the metal may serve as a conductive electrode. When non-conductive substrates are employed, they may be covered with conductive foil, metal plating, or other conductive materials, such as doped tin oxide and other semiconductor materials. Silicon and glass are preferred materials since these may be micromachined and otherwise processed employing techniques common to the processing of semiconductors and integrated circuits. Glass substrates with transparent indium tin oxide electrodes are quite useful as these allow inspection by optical techniques.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An electrode system for protein patterning, the electrode comprising:
    a first electrode containing structure comprising a patterned conductive layer;
    a non-adherent layer disposed over the patterned conductive layer, the non-adherent layer having a non-adherent surface that is hydrophobic and non-polar;
    a second electrode containing structure disposed over the non-adherent layer; and
    a power supply in communication with the first electrode containing structure and the second electrode containing structure,
    wherein the first electrode containing structure, the non-adherent layer, and the second electrode containing structure are positioned relative to each other to allow contacting of the non-adherent layer with a protein composition in a solution; and
    wherein the non-adherent layer is capable of acquiring an electric charge or of being polarized such that application of a potential difference between the first electrode containing structure and the second electrode containing structure renders the non-adherent layer adherent to protein molecules in the solution until the potential difference between the first electrode containing structure and the second electrode containing structure is reversed.

2. The electrode system of claim 1 wherein the non-adherent surface is a polymer surface.

3. The electrode system of claim 2 wherein the non-adherent surface comprises a fluorinated polymer surface or a polyolefin polymer.

4. The electrode system of claim 1 wherein the non-adherent surface comprises a surface selected from the group consisting of glass surfaces, organopolysiloxane surfaces, metal surface, and combinations thereof.

5. The electrode system of claim 4 wherein the non-adherent surface is treated with a coating agent to make proteins non-adherent thereto.

6. The electrode system of claim 5 wherein the coating agents comprise a component selected from the group consisting of fluorinated hydrocarbon-functional silanes, alkylsilanes, and the like.

7. The electrode system of claim 1 wherein the first conductive electrode containing structure is positioned below the protein non-adherent layer and the second electrode containing structure is positioned above the non-adherent layer to form a channel adjacent to the non-adherent surface of the non-adherent layer.

8. The electrode system of claim 1 wherein the power supply is operable to reverse the adhesion of protein to the non-adherent surface.

9. The electrode system of claim 8 wherein the power supply is operable to decrease or reverse the potential difference between the first and second electrode containing structures.

10. The electrode system of claim 1 wherein the first and second electrode containing structures each independently comprise:
    a non-conducting substrate; and
    a patterned conductive layer disposed over the substrate.

11. The electrode system of claim 10 wherein the patterned conductive layer comprises a component selected from the group consisting of metals, conductive metal oxides, and combinations thereof.

12. A multilayer or multichannel protein patterning system comprising the electrode system of claim 1.

* * * * *

UNITED STATES PATENT AND TRADEMARK OFFICE
CERTIFICATE OF CORRECTION

PATENT NO.        : 7,615,369 B2                                              Page 1 of 1
APPLICATION NO. : 11/233975
DATED             : November 10, 2009
INVENTOR(S)       : Lin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 415 days.

Signed and Sealed this

Nineteenth Day of October, 2010

David J. Kappos
*Director of the United States Patent and Trademark Office*